United States Patent [19]

Antberg et al.

[11] Patent Number: 5,071,808
[45] Date of Patent: Dec. 10, 1991

[54] PROCESS FOR THE PREPARATION OF A HETEROGENEOUS METALLOCENE CATALYST COMPONENT

[75] Inventors: Martin Antberg, Hofheim am Taunus; Ludwig Böhm, Hattersheim am Main; Jürgen Rohrmann, Liederbach, all of Fed. Rep. of Germany

[73] Assignee: Hoechst Aktiengesellschaft, Frankfurt am Main, Fed. Rep. of Germany

[21] Appl. No.: 444,105

[22] Filed: Nov. 30, 1989

[30] Foreign Application Priority Data

Dec. 3, 1988 [DE] Fed. Rep. of Germany ....... 3840772

[51] Int. Cl.$^5$ .................... C08F 4/656; C08F 10/02
[52] U.S. Cl. ................................ 502/107; 502/104; 502/117; 502/125; 526/127; 526/160; 526/308; 526/352; 556/11
[58] Field of Search .............................. 502/104, 107

[56] References Cited

U.S. PATENT DOCUMENTS

| 3,208,985 | 9/1965 | Piekarski et al. | 526/126 |
| 3,740,384 | 6/1973 | Ballard et al. | 526/126 |
| 4,292,253 | 9/1981 | Ozin et al. | 260/429.5 |
| 4,522,982 | 6/1985 | Ewen. | |
| 4,542,199 | 9/1985 | Kaminsky et al. | |
| 4,808,561 | 2/1989 | Welborn, Jr. | |
| 4,945,076 | 1/1990 | Piotrowski et al. | 502/117 |

FOREIGN PATENT DOCUMENTS

| 0128045 | 12/1984 | European Pat. Off. . |
| 0171307 | 2/1986 | European Pat. Off. . |
| 0206794 | 12/1986 | European Pat. Off. . |
| 3718888 | 12/1988 | Fed. Rep. of Germany . |

OTHER PUBLICATIONS

R. Jackson, J. Ruddlesden, D. Thompson and R. Whelan, "Silica-Supported Analogues of Titanocene", *Journal of Organometallic Chemistry*, vol. 125, Elsevier Sequoia S.A. (Laussane, Netherlands) (1977), pp. 57–62.

*Primary Examiner*—Edward J. Smith

[57] ABSTRACT

The invention relates to a process for the preparation of a heterogeneous metallocene catalyst component from a suitably substituted metallocene of the sub-group 4 of the Periodic Table of the Elements and from poly(methylhydrogensiloxane) under the concomitant action of a catalyst. The metallocene component and a suitable aluminoxane can be used as catalyst for the polymerization of 1-olefins, cyclic olefins, diolefins and cyclic diolefins.

8 Claims, No Drawings

PROCESS FOR THE PREPARATION OF A HETEROGENEOUS METALLOCENE CATALYST COMPONENT

DESCRIPTION

The present invention relates to a process for the preparation of heterogeneous metallocene catalyst components using poly(methylhydrogensiloxane).

Metallocenes of transition metals are known as catalyst components (cf. U.S. Pat. Nos. 4,522,982, 4,542,199 and EP 128,045). Together with aluminoxanes, they form homogeneous transition metal catalysts which are soluble in aromatic and aliphatic hydrocarbons. These catalysts are very active. Soluble catalysts are disadvantageous if they are to be employed in existing industrial plants since the latter are generally designed for the use of heterogeneous catalyst systems. It was therefore desirable to find metallocene catalysts which can be used as insoluble solids in the form of a suspension.

Metallocene catalysts in which a zirconocene or titanocene component and an aluminoxane are applied together from a solution onto a silicate support are known (cf. EP 206,794). However, this catalyst system is not very active. In addition, the catalyst components are not anchored to the support sufficiently firmly and can thus be extracted during the polymerization.

In addition, it is known that metallocene compounds containing silyl ether radicals can be applied to silicate supports with formation of siloxane bridges (cf. DE 3,718,888). For this, it is necessary to remove adsorptively bound water from the support material by drying for several hours at a maximum temperature of 800° C. A certain hydroxyl group content is thus established, which is determined analytically using n-butyl-magnesium chloride. The support conditioned in this way must be stored under an inert gas with exclusion of air and water.

It has now been found that the abovementioned disadvantages can be avoided if a suitably substituted metallocene compound is reacted with a poly(methylhydrogensiloxane) with hydrosilylation catalysis.

The invention thus relates to the process described in the claims.

To prepare the heterogeneous metallocene catalyst component according to the invention, compounds of the formula I

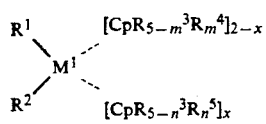

or of the formula II

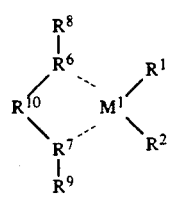

are used in which $M^1$ is titanium, zirconium or hafnium, preferably zirconium, and $C_p$ denotes a cyclopentadienyl radical.

$R^1$ and $R^2$ are identical or different and denote a hydrogen atom, a halogen atom, a $C_1$–$C_{10}$-alkyl group, a $C_1$–$C_{10}$-alkoxy group, a $C_7$–$C_{20}$-arylalkyl group, a $C_6$–$C_{10}$-aryl group, a $C_6$–$C_{10}$-aryloxy group, preferably an alkyl group or a halogen atom, in particular a chlorine atom. $R^1$ and $R^2$ may also be linked to one another and may form a metallocycle together with $M^1$.

$R^3$ denotes a hydrogen atom, a halogen atom, a $C_1$–$C_{10}$-alkyl group, a $C_6$–$C_{10}$-aryl group, a $C_7$–$C_{20}$-arylalkyl group, a $C_1$–$C_{10}$-fluoroalkyl group or an organometalic radical such as $C_1$–$C_{10}$-trialkylsilyl, $C_6$–$C_{10}$-aryl-$C_1$–$C_{10}$-dialkylsilyl, $C_1$–$C_{10}$-alkyl-$C_6$–$C_{10}$-diarylsilyl or $C_6$–$C_{10}$-triarylsilyl. $R^3$ is preferably a hydrogen atom or a methyl group, in particular a hydrogen atom.

$R^4$ and $R^5$ are identical or different and denote a $C_2$–$C_{10}$-alkenyl group, a $C_8$–$C_{12}$-alkenylaryl group, a $C_2$–$C_{10}$-alkenoxy group, a $C_2$–$C_8$-alkenyl-$C_1$–$C_8$-dialkylsilyl group, a $C_2$–$C_8$-alkenyl-$C_6$–$C_{10}$-diarylsilyl group or a $C_2$–$C_8$-alkenyl-$C_1$–$C_8$-alkyl-$C_6$–$C_{10}$-arylsilyl group. $R^4$ and $R^5$ are preferably a $C_2$–$C_{10}$-alkenyl group or a $C_2$–$C_8$-alkenyl-$C_1$–$C_8$-dialkylsilyl group.

$R^6$ and $R^7$ are identical or different and denote a cyclopentadienyl, indenyl or fluorenyl radical, it being possible for the five-membered rings mentioned to form a sandwich structure together with $M^1$. $R^6$ and $R^7$ are preferably indenyl radicals.

$R^8$ and $R^9$ are identical or different, denote substituents of the five-membered rings $R^6$ and $R^7$ mentioned in the 3-position and are a $C_2$–$C_{10}$-alkenyl group or an organometallic radical, such as, for example, a $C_2$–$C_{10}$-alkenyl-$C_1$–$C_{10}$-dialkylsilyl group, a $C_1$–$C_{10}$-alkyl-$C_2$–$C_{10}$-dialkenylsilyl group, a $C_2$–$C_{10}$-alkenyl-$C_6$–$C_{10}$-diarylsilyl group or a $C_6$–$C_{10}$-aryl-$C_2$–$C_{10}$-dialkenylsilyl group, preferably an alkenyl or alkenyldialkylsilyl group, in particular a butenyl or alkyldimethylsilyl group.

$R^{10}$ has the meaning shown in the formulae III–VII

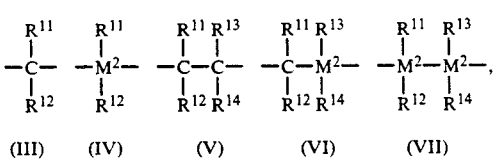

where $M^2$ is silicon, germanium or tin, preferably silicon, and $R^{11}$, $R^{12}$, $R^{13}$ and $R^{14}$ are identical or different and denote a hydrogen atom, a halogen atom, a $C_1$–$C_{10}$-alkyl group, a $C_1$–$C_{10}$-fluoroalkyl group, a $C_6$–$C_{10}$-aryl group, a $C_6$–$C_{10}$-fluoroaryl group, a $C_1$–$C_{10}$-alkoxy group, a $C_6$–$C_{10}$-aryloxy group or a $C_7$–$C_{20}$-arylalkyl group, preferably a dialkylsilyl group or a 1,2-alkanediyl group, in particular a dimethylsilyl group or 1,2-ethanediyl group.

$R^{11}$ and $R^{12}$ or $R^{13}$ and $R^{14}$ can be linked to one another to form spirocyclic systems, such as

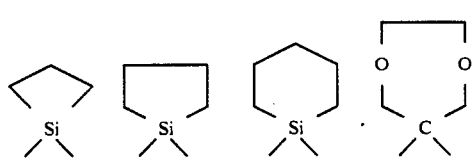

just as $R^{11}$ and $R^{13}$ or $R^{12}$ and $R^{14}$ can form the ring system below

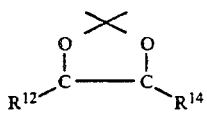

x is zero or 1, preferably zero.

m and n are identical or different and denote a number from zero to 5, preferably 1 to 3, in particular 1.

Examples of suitable metallocene compounds of the formula I are

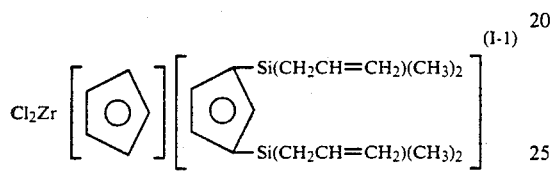

(I-1)

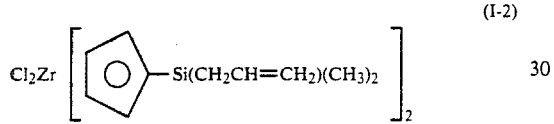

(I-2)

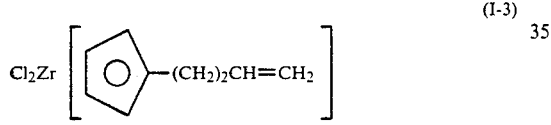

(I-3)

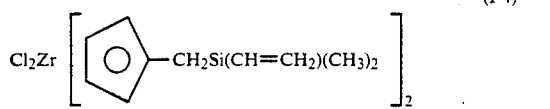

(I-4)

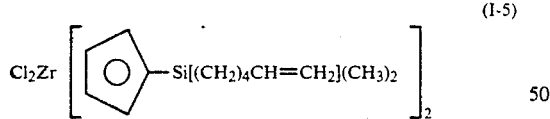

(I-5)

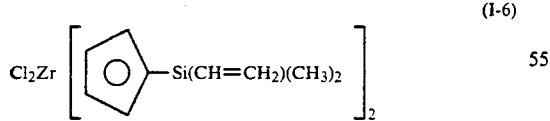

(I-6)

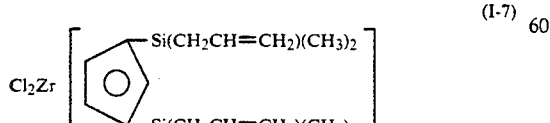

(I-7)

Examples of suitable metallocene compounds of the formula II are

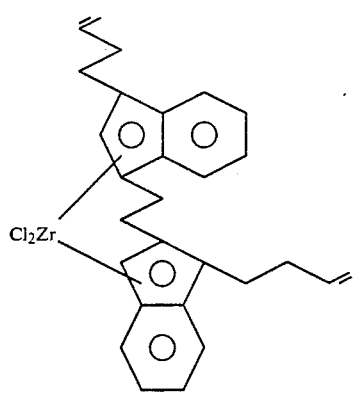

(II-1)

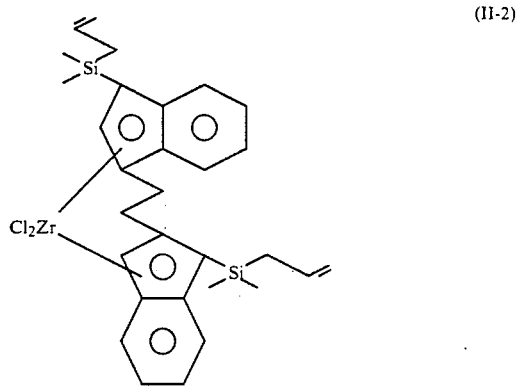

(II-2)

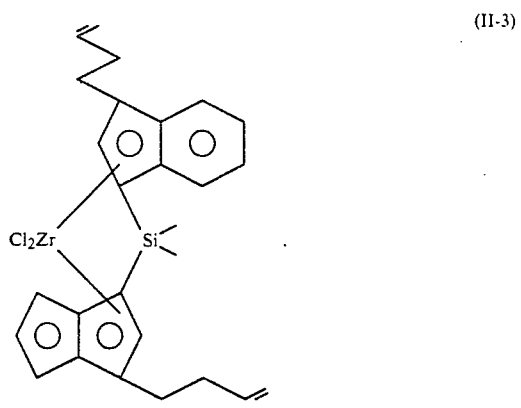

(II-3)

The metallocenes contain at least two olefinic functions which react further in a hydrosilylation reaction; catalyzed by a compound of sub-group 8 of the Periodic Table of the Elements, for example osmium, iridium and platinum, preferably by platinum, in particular by hexachloroplatinic acid hexahydrate, with a poly(methylhydrogensiloxane), for example $(CH_3)_3SiO[Si(CH_3)HO]_{3.5}Si(CH_3)_3$, to form a heterogeneous polymerization catalyst in accordance with the equation below:

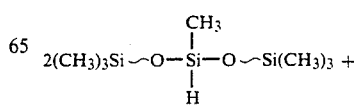

-continued

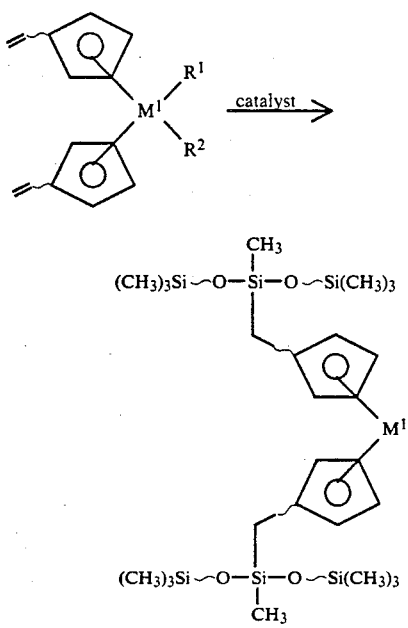

For heterogenization, the metallocene is dissolved in a solvent, for example an aliphatic or cycloaliphatic hydrocarbon, for example pentane or cyclohexane, or in an aromatic hydrocarbon, for example toluene or xylene, or in an ether, for example diethyl ether, the poly(methylhydrogensiloxane) and the hydrosilylation catalyst are added, and the mixture is warmed for 5 to 120 minutes, preferably 10 to 30 minutes, at 20° to 90° C., preferably 30° to 80° C. A gray precipitate then forms and is filtered off, washed and dried. The course of the reaction can be monitored by IR spectroscopy on the basis of the C=C and Si—H vibration bands. The heterogenous catalyst obtained according to the invention can be employed for the polymerization of 1-olefins of the formula $$R^{15}-CH=CH_2.$$

in which $R^{15}$ denotes hydrogen, a straight-chain or branched alkyl group, for example ethylene, propylene or 4-methyl-1-pentene.

In addition, the catalyst can also be employed for the polymerization of the cyclic olefins, such as, for example, cyclopentene, cyclohexene, norbornene, diolefins and cyclic diolefins.

In this case, an aluminoxane, whose synthesis is known, can be used for the polymerization in addition to the metallocene.

The invention is illustrated by means of the Examples below.

EXAMPLE 1

2.89 g (24.04 mmol) of $C_5H_4-(CH_2)_2CH=CH_2$, dissolved in 50 cm³ of THF, are added dropwise over the course of 3 hours to 1.3 g (32.41 mmol) of potassium hydride in 20 cm³ of THF at room temperature, and the batch was subsequently stirred overnight. Unreacted potassium hydride is filtered off, washed with small portions of ether, dried in vacuo and weighed. 0.78 g (19.45 mmol) were obtained.

12.96 mmol of $K^+[C_5H_4-(CH_2)_2CH=CH_2]^-$  were produced.

The cyclopentadienide solution filtered off was added dropwise over the course of 1.5 hours to a suspension of 2.46 g (6.52 mmol) of $Cl_4Zr(THF)_2$ in 20 cm³ of THF at −10° C. After the mixture had been stirred at room temperature for 4 hours, the batch was filtered, the filtrate was evaporated, and the residue was extracted using a hydrocarbon. After the combined extracts had been concentrated, the precipitate which formed at −40° C. was removed and dried in vacuo.

Yield: 1.5 g (3.75 mmol△57%) of $Cl_2Zr[C_5H_4-(CH_2)_2CH=CH_2]_2$

The compound exhibited a $^1H$ NMR spectrum which conformed to expectations and a correct elementary analysis.

EXAMPLE 2

The procedure followed was analogous to Example 1, but with the difference that 0.87 g (21.69 mmol) of potassium hydride and 3.56 g (21.67 mmol) of $C_5H_4-Si(CH_3)_2CH_2CH=CH_2$ were employed. The conversion of potassium hydride was complete and the amount of $Cl_4Zr(THF)_2$ was 4.08 g (10.82 mmol).

Yield: 2.44 g (4.99 mmol△46%) of $Cl_2Zr[C_5H_4-Si(CH_3)_2=CH_2=CH=CH_2]_2$

The elementary analysis and the $^1H$ NMR spectrum conformed to expectations.

EXAMPLE 3

10.16 g (22.35 mmol) of 1,2-[1,1'bis(3-allyldimethylsilylindenyl)ethane] were dissolved in 100 cm³ of THF, and 27.95 cm³ of a 1.6N butyllithium/hexane solution (44.72 mmol) were added dropwise at room temperature over the course of 2 hours. After the batch had been stirred at about 60° C. for 4 hours, it was evaporated, the residue was suspended in a hydrocarbon, the suspension was filtered, and the solid was washed, dried and weighed. 9.39 g (20.12 mmol 94%) of dilithium salt were produced. The dilithium salt was suspended in 100 cm³ of toluene, and 8.2 g (21.74 mmol) of $Cl_4Zr(THF)_2$ in 100 cm³ of THF were added at room temperature over the course of 2 hours. After the batch had been stirred overnight, it was evaporated, the residue was extracted with a hydrocarbon, the extracts were filtered, and the combined filtrates were evaporated.

Yield: 5 g (8.13 mmol △40%) of ethylenebis[1-(3-allyl-dimethylsilylindenyl)zirconium] dichloride.

The compound exhibited a correct elementary analysis.

EXAMPLE 4

0.98 g (2 mmol) of the compound having the formula I-2 were dissolved in 12 cm³ of toluene, and 0.52 g (0.23 mmol) of poly(methylhydrogensiloxane) and 0.02 g of $H_2PtCl_6.6H_2O$ were added. After the mixture had been warmed for a few minutes, a dark gray, solid phase formed. The supernatant solution no longer exhibited Si—H vibration bands in the IR spectrum. The precipitate was therefore separated off, and washed thoroughly with toluene in order to remove any unreacted, adsorptively bound complex. The product was subsequently dried in vacuo. The residue, examined by elementary analysis, contained 10.2% of Zr.

EXAMPLE 5

The procedure followed was analogous to Example 4, but with the difference that 0.83 g (1.70 mmol) of the compound having the formula I-2, 0.45 g (0.20 mmol) of poly(methylhydrogensiloxane) and 0.21 g of $H_2PtCl_6 \cdot 6H_2O$ were employed. The residue, examined by elementary analysis, contained 8.4% of Zr.

EXAMPLE 6

The procedure followed was analogous to Example 4, but with the difference that 1.2 g (3 mmol) of the compound having the formula I-3, 0.74 g (0.33 mmol) of poly(methylhydrogensiloxane) and 0.15 g of $H_2PtCl_6 \cdot 6H_2O$ were employed. The residue, examined by elementary analysis, contained 9.3% of Zr.

EXAMPLE 7

900 cm$^3$ of a diesel oil fraction (b.p.=100°-120° C.) were placed in a 1.5 dm$^3$ steel autoclave and heated to 70° C. The reactor was charged with a toluene solution of 0.25 g of methylaluminoxane and 0.01 mmol of the heterogeneous catalyst from Example 4. Ethylene was then injected to a final pressure of 7 bar, and the mixture was polymerized for 2 hours. The catalyst residues in the suspension were decomposed using aqueous HCl. The polymer was isolated, washed with acetone and dried. 5.1 g of polyethylene were obtained. This corresponds to an activity of 255 g of polymer/mmol of Zr.h (further data in the Table).

EXAMPLE 8

600 cm$^3$ of a diesel oil fraction (b.p.=100°-120° C.) and 300 cm$^3$ of cyclopentene were placed in a 1.5 dm$^3$ steel autoclave heated to 60° C. The reactor was charged with a toluene solution of 0.25 g of methylaluminoxane and 0.01 mmol of the heterogeneous catalyst from Example 4. After ethylene had been injected to 7 bar, the batch was polymerized for 2 hours. The polymer solution was added to twice the amount of a methanol/acetone mixture. The ethylene-cyclopentene copolymer which precipitated was isolated and dried. The yield was 4.2 g, corresponding to an activity of 210 g of polymer/mmol of Zr.h (further data in the Table).

EXAMPLE 9

900 cm$^3$ of cyclopentene were placed in a 1.5 dm$^3$ steel autoclave, which was charged with 0.25 g of methylaluminoxane and 0.01 mmol of the heterogeneous catalyst from Example 4. After the batch had been polymerized for 2 hours at 60° C., the polymer solution was worked up as in Example 8. The yield of polymer was 1.6 g, corresponding to an activity of 80 g of polymer/mmol of Zr.h (further data in the Table).

Examples 10 and 11 were carried out in corresponding manner to the data in the Table.

We claim:
1. A process for the preparation of a heterogeneous metallocene catalyst component from a metallocene of the formula I

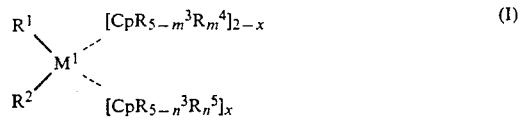

or of the formula II

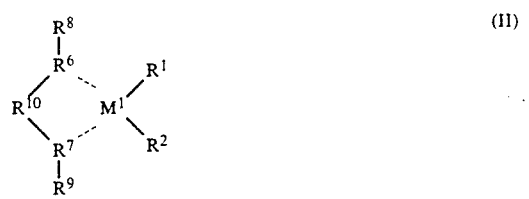

wherein said metallocenes contain at least two olefinic functions, and in which $M^1$ is titanium, zirconium or hafnium, and Cp denotes a cyclopentadienyl radical, $R^1$ and $R^2$ are identical or different and denote a hydrogen atom, a halogen atom, a $C_1$-$C_{10}$-alkyl group, a $C_1$-$C_{10}$-alkoxy group, a $C_7$-$C_{20}$-arylalkyl group, a $C_6$-$C_{10}$-aryl group or a $C_6$-$C_{10}$-aryloxy group, $R^1$ and $R^2$ may also be linked to one another and may form a metallocycle together with $M^1$, $R^3$ denotes a hydrogen atom, a halogen atom, a $C_1$-$C_{10}$-alkyl group, a $C_6$-$C_{10}$-aryl group, a $C_7$-$C_{20}$-arylalkyl group, a $C_1$-$C_{10}$-fluoroalkyl group or an organometallic radical, $R^4$ and $R^5$ are identical or different and denote a $C_2$-$C_{10}$-alkenyl group, a $C_2$-$C_{12}$-alkenylaryl group, a $C_2$-$C_{10}$-alkenoxy group, a $C_2$-$C_8$-alkenyl-$C_1$-$C_8$-dialkylsilyl group, a $C_2$-$C_8$-alkenyl-$C_6$-$C_{10}$-di-arylsilyl group or a $C_2$-$C_8$-alkenyl-$C_1$-$C_8$-alkyl-$C_6$-$C_{10}$-arylsilyl group, $R^6$ and $R^7$ are identical or different and denote a cyclopentadienyl, indenyl or fluorenyl radical, it being possible for the five-membered rings mentioned to form a sandwich structure together with $M^1$;

$R^8$ and $R^9$ are identical or different, are substituents of the five-membered rings $R^6$ and $R^7$ mentioned in the 3-position and denote a $C_2$-$C_{10}$-alkenyl group or an organometallic radical, $R^{10}$ has the meaning shown in the formulae III-VII

TABLE

| | | Polymerization data of Examples 7-11 | | | | | |
|---|---|---|---|---|---|---|---|
| Ex. | Monomers | Catalyst/ cocatalyst | Polymerization as in Example | Temp. °C. | Yield g | VN cm$^3$/g | $M_w/M_n$ | Incorporation rate % by weight |
| 7 | Ethylene | 0.01 mmol from Ex. 4/ 0.25 g MAO | 7 | 70 | 5.1 | 831 | — | — |
| 8 | Ethylene/ cyclopentene | 0.01 mmol from Ex. 4/ 0.25 g MAO | 8 | 60 | 4.2 | 150 | 3.3 | 15% |
| 9 | Cyclopentene | 0.01 mmol from Ex. 6/ 0.25 g MAO | 9 | 60 | 1.6 | 60 | 3.2 | — |
| 10 | Cyclooctene | 0.01 mmol from Ex. 4/ 0.25 g MAO | 9 | 60 | 1.2 | 20 | 3.5 | — |
| 11 | Ethylene/ cycloheptene | 0.01 mmol from Ex. 6/ 0.25 g MAO | 8 | 60 | 3.8 | 120 | 3.6 | 11% |

MAO = methylaluminoxane

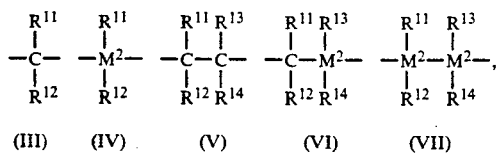

where

M² is silicon, germanium or tin and $R^{11}$, $R^{12}$, $R^{13}$ and $R^{14}$, are identical or different and denote a hydrogen atom, a halogen atom, a $C_1$-$C_{10}$-alkyl group, a $C_1$-$C_{10}$-fluoroalkyl group, a $C_6$-$C_{10}$-aryl group, a $C_6$-$C_{10}$-fluoroaryl-group, a $C_1$-$C_{10}$-alkoxy group, a $C_6$-$C_{10}$-aryloxy group or a $C_7$-$C_{20}$-arylalkyl group, $R^{11}$ and $R^{12}$, $R^{13}$ and $R^{14}$, $R^{11}$ and $R^{13}$ or $R^{12}$ and $R^{14}$ can form a ring system together with the atoms linking them, x is zero or 1, m and n are identical or different and denote a number from zero to 5, and a poly(methylhydrogensiloxane), which process is carried out at a temperature of 20° C.-90° C. and within 5 to 120 minutes using a hydrosilylation catalyst.

2. The process as claimed in claim 1, wherein the hydrosilylation catalyst is a compound of sub-group 8 of the Periodic Table of the Elements.

3. The process as claimed in claim 1, wherein the hydrosilylation catalyst is $H_2PtCl_6 \cdot 6H_2O$.

4. The process as claimed in claim 1, which comprises the steps of:
   a. dissolving said metallocene of formula I or II in an aliphatic, cycloaliphatic or aromatic hydrocarbon or in an ether, thereby obtaining a metallocene-containing solution,
   b. adding the poly(methylhydrogensiloxane) and the hydrosilylation catalyst to the metallocene-containing solution and warming said solution for 5 to 120 minutes to a temperature of 30° to 80° C., thereby forming the heterogeneous metallocene catalyst component as a precipitate, and
   c. isolating the precipitate from said solution.

5. The process as claimed in claim 4, wherein the hydrosilylation catalyst is a compound of sub-group 8 of the Periodic Table of the Elements.

6. The process as claimed in claim 5, wherein the hydrosilylation catalyst is $H_2PtCl_6 \cdot 6H_2O$.

7. The process as claimed in claim 4, wherein said solution is warmed for 10 to 30 minutes.

8. The process of claim 1, wherein said organometallic radical of $R^3$ is $C_1$-$C_{10}$-trialkylsilyl, $C_6$-$C_{10}$-aryl-$C_1$-$C_{10}$-dialkylsilyl, $C_1$-$C_{10}$-alkyl-$C_6$-$C_{10}$-diarylsilyl or $C_6$-$C_{10}$-triarylsilyl.

* * * * *